US00PP12197P2

(12) United States Plant Patent
Osiecki

(10) Patent No.: US PP12,197 P2
(45) Date of Patent: Nov. 13, 2001

(54) ANTHURIUM PLANT NAMED 'LOLA'

(75) Inventor: Marian Wincenty Osiecki, Marianna, FL (US)

(73) Assignee: Oglesby Plants International, Inc., Altha, FL (US)

( * ) Notice: Subject to any disclaimer, the term of this patent is extended or adjusted under 35 U.S.C. 154(b) by 0 days.

(21) Appl. No.: 09/569,367

(22) Filed: May 11, 2000

(51) Int. Cl.[7] ..... A01H 5/00

(52) U.S. Cl. ..... Plt./369

(58) Field of Search ..... Plt./369, 367

*Primary Examiner*—Bruce R. Campell
*Assistant Examiner*—Michelle Kizilkaya

(57) ABSTRACT

A new distinct cultivar of Anthurium is provided. It is a medium size plant, suitable for production in 15-cm to 20-cm containers, with vigorous growth; full and symmetrical growth habit; early and abundant branching; abundant and year-round flowering. Exceptionally dark red and glossy spathes are held high above foliage on straight peduncles; spadices are yellow when young and white at maturity.

3 Drawing Sheets

BACKGROUND OF THE INVENTION

This invention relates to a new and distinct cultivar of Anthurium plant, botanically known as Anthurium hybrid, and hereinafter referred to by the cultivar name Lola.

The new cultivar is a product of a planned breeding program conducted by the Inventor in Altha, Fla. The objective of the program was to develop a well branching pot Anthurium cultivar with dark red, shiny spathes well visible above foliage and with spadices contrasting with spathes.

The new Anthurium was discovered and selected by the Inventor in 1993 as a seedling within the progeny of a cross made in 1992 in a controlled environment in Altha, Fla. The female parent was a seedling of *Anthurium andreanum*, discovered at Anthuriums of Hawaii in Hawaii, and referred to by the name Yogi Mini Red (not patented). The male parent was a selected clone of Anthurium hybrid cultivar Ruth Morat, disclosed in U.S. Plant Pat. No. 8,540, a/k/a Lady Ruth™.

Asexual propagation of 'Lola' by means of tissue culture in Altha, Fla. has established than the unique characteristics of this new cultivar are in fact stable and reproduced true to type in successive generations.

SUMMARY OF THE INVENTION

The new Anthurium cultivar has not been observed under all possible environmental conditions. The phenotype may vary somewhat with variations in environment and/or horticultural practices such as temperature, light intensity, day length, fertilization, irrigation, propagation procedures etc., without any variance in genotype.

The following traits have been repeatedly observed and in combination distinguish 'Lola' as a new and distinct cultivar of pot Anthurium:

1. Medium size plant, appropriate for 15-cm to 20-cm containers;

2. Symmetrical, rounded and full growth habit;

3. Vigorous growth;

4. Early and abundant branching;

5. Abundant and year-round flowering;

6. Exceptionally dark red, very glossy spathes, becoming darker with age and maintaining glossiness long past inflorescence maturity;

7. Spathes held high above foliage, mostly in the center of the plant on almost vertical, usually straight peduncles;

8. Spadices sharply contrasting with spathes, yellow when young, white when mature.

Plants of 'Lola' are distinguished from plants of the female parent, seedling Yogi Mini Red, by its larger size; more vigorous growth; more abundant branching and flowering; smaller spathes, that are of much darker red color.

Plants of 'Lola' are distinguished from plants of the male parent, cultivar Ruth Morat, by its smaller size; slightly later flowering; slightly longer crop time; smaller and slightly lighter green leaves; smaller, less elongated, much darker red and glossier spathes; spadices that are yellow when young and white when mature, as opposed to pink-purple spadices of 'Ruth Morat'.

The new cultivar can be compared to the known Anthurium cultivars: '75-10', disclosed in U.S. Plant Pat. No. 9,355, a/k/a Red Hot™ and 'A8', disclosed in U.S. Plant Pat. No. 10,551, a/k/a Nicoya™. The comparisons were made on plants of the same age, grown side-by-side under the same greenhouse conditions in Altha, Fla.

Plants of the new Anthurium cultivar differ from plants of the cultivar 75-10 in the following characteristics:

1. Plants of 'Lola' start flowering slightly later and have slightly longer crop time than plants of '75-10'.

2. Inflorescences of plants of 'Lola' are of a good quality from the onset of flowering, whereas several first spathes produced by plants of '75-10'. are very small and deformed.

3. Spathes of young plants of 'Lola' are larger than spathes of young plants '75-10'.

4. Spathes of 'Lola' are much darker red and glossier than spathes of '75-10'.

5. Spathes of 'Lola' are non-puckered and convex or cupped, whereas spathes of '75-10' are puckered and wavy.

6. Spadices of 'Lola' are yellow when young and white when mature, whereas spadices of '75-10' are purple from the time of spathe unrolling.

7. Spadices of 'Lola' are straight, whereas spadices of '75-10' are curved.

8. Petioles and peduncles of 'Lola' are predominantly green, whereas petioles and peduncles of '75-10' are predominantly red-brown.

9. Mature leaves of 'Lola' are slightly lighter green than mature leaves of '75-10'.

10. Young leaves of 'Lola' are light green, whereas young leaves of '75-10' are brownish green.

11. Veins of mature leaves of 'Lola' have very little to no brownish anthocyanin coloration, whereas veins of mautre leaves of '75-10' usually have pronounced anthocyanin coloration.

12. Roots of 'Lola' are cream to light brown, whereas many roots of '75-10' are dark pink.

Plants of the new Anthurium cultivar differ from plants of the cultivar A8 in the following characteristics:

1. Plants of 'Lola' start flowering later and have longer crop time than plants of 'A8'.

2. Plants of 'Lola' branch slightly more freely than plants of 'A8'.

3. Spathes of 'Lola' are smaller, more ovate (less deltoid) and situated higher above foliage than spathes of 'A8'.

4. Spathes of 'Lola' are very dark red, whereas spathes of 'A8' are bright red.

5. Spathes of 'Lola' are non-puckered, convex or cupped, whereas spathes of 'A8' are approximately flat and usually slightly puckered.

6. Spadices of 'Lola' are smaller than spadices of 'A8'.

7. Spadices of 'Lola' are yellow when young and white when mature, whereas spadices of 'A8' are pale pink-purple in color.

BRIEF DESCRIPTION OF THE PHOTOGRAPHS

The accompanying photographs illustrate the appearance of the new Anthurium cultivar, showing the colors as true as it is reasonably possible in color reproductions of this type. Colors in the photographs may appear slightly different from the color values cited in the botanical description, which accurately describe the actual colors of the plants of the new cultivar. The plant of 'Lola' depicted in the photographs was approximately 14.5 month from planting a single tissue culture-produced microcutting, and was grown in a 15-cm container.

In the photographs:

BOTANICAL DESCRIPTION OF THE NEW CULTIVAR

Figure 1:
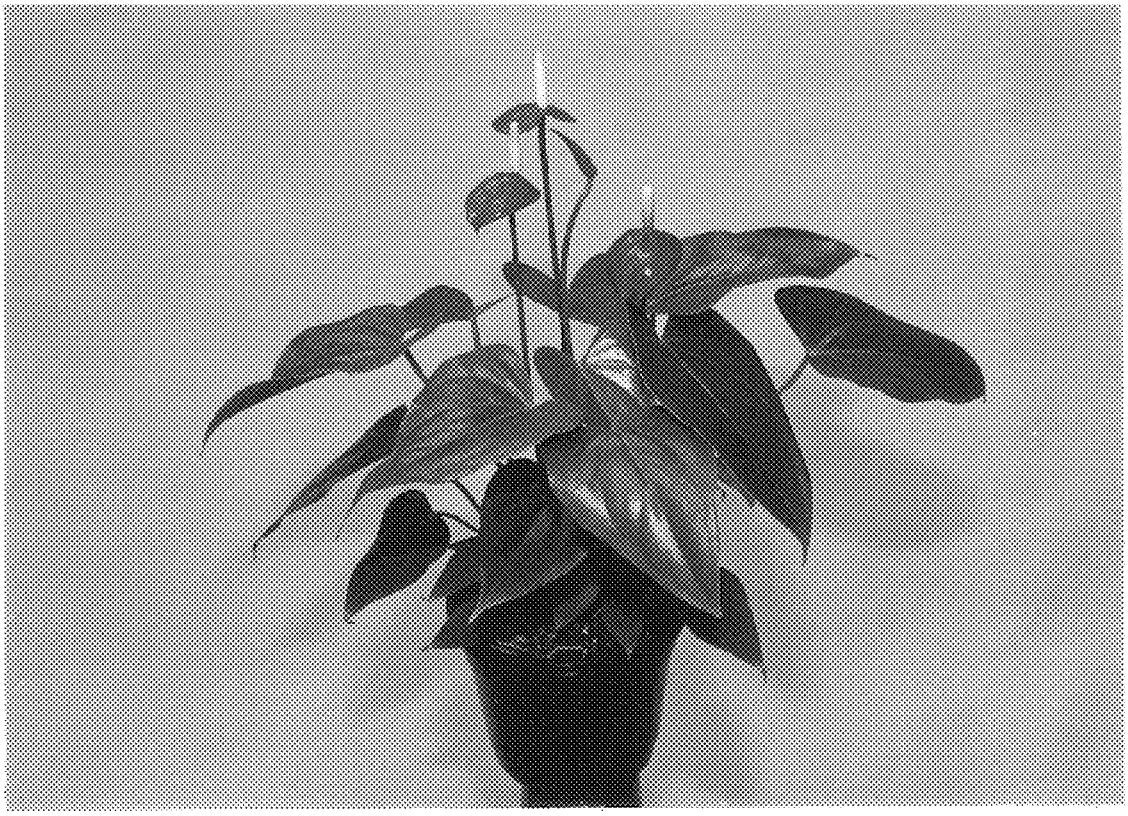
FIG. 1 depicts the whole plant.
Figure 2:
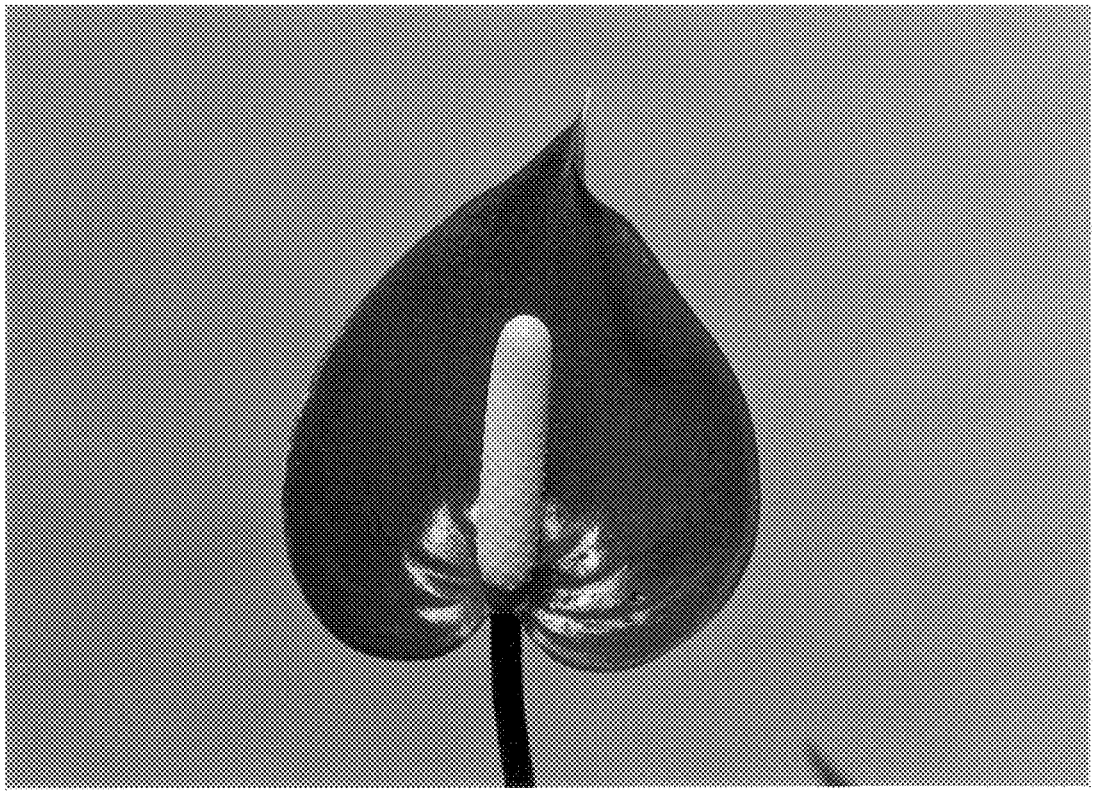
FIG. 2 illustrates the mature inflorescence.
Figure 3:
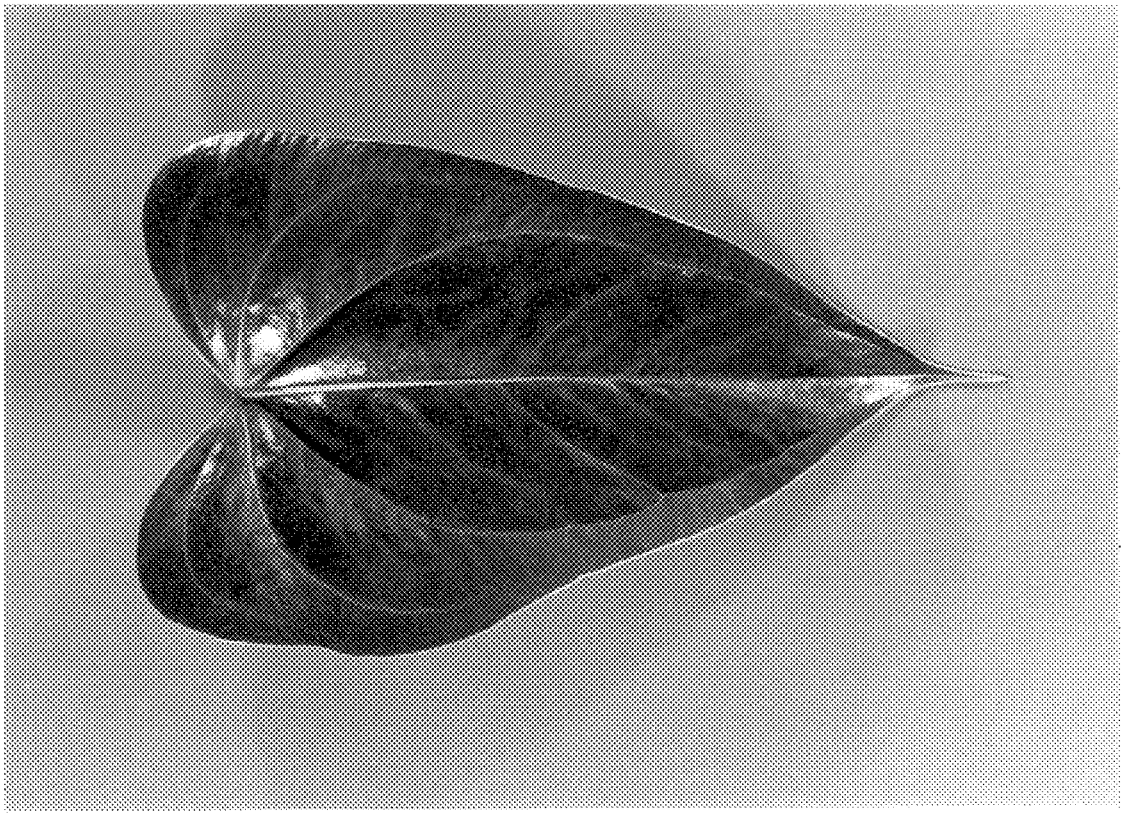
FIG. 3 illustrates the adaxial side of a mature leaf.

The following observations and measurements were recorded in April 2000, on plants grown in a polycarbonate-covered greenhouse in Altha, Fla. under conditions which closely approximate those used in commercial horticultural practice. During growth of these plants day temperature in the greenhouse ranged between 23 and 28° C., night temperature ranged between 20 and 23° C., and light level ranged between 800 and 1500 foot-candles. Plants used for these observations were grown as single plants in 15-cm containers and were about 14.5 months from planting tissue culture-produced microcuttings.

Mature, fully developed plant organs were used for the following observations and measurements unless otherwise indicated. Numerical measurements represent means from typical plants of 'Lola'. Color references are made to the R.H.S. Color Chart, except where general color terms of ordinary significance are used. Color values were determined under natural light of approximately 950 to 1400 foot-candles.

Botanical classification: Anthurium hybrid cultivar Lola.

Parentage:

*Female parent.*—*Anthurium andreanun* seedling Yogi Mini Red (not patented).

*Male parent.*—Selected clone of Anthurium hybrid cultivar Ruth Morat, disclosed in U.S. Plant Pat. No. 8,540, a/k/a Lady Ruth™.

Propagation:

*Type.*—Plant tissue culture.

*Time to produce a rooted liner.*—Summer: About 16 to 18 weeks at about 25 to 30° C. soil temperature. Winter: About 18 to 20 weeks at about 22 to 27° C. soil temperature.

Plant description:

*Growth habit.*—Medium size, rounded, symmetrical, well-branched, full. Appropriate for 15-cm to 20-cm containers.

*Plant size.*—Height, soil level to top of inflorescences: About 32.6 cm. Height, soil level to top of leaf canopy: About 23.5 cm. Diameter (area of spread): About 44.0 cm.

*Plant vigor.*—Vigorous.

*Crop time.*—About fourteen months are needed to produce a finished plant in a 15-cm container from a single tissue culture-produced microcutting.

Foliage description:

*Petiole.*—Size: About 17.3 cm long, about 3.3 mm in diameter immediately below geniculum. Geniculum: About 2.2 cm long, about 3.7 mm in diameter at the base. Not very prominent. Petiole wings: About 1.4 cm long, about 4.1 mm wide. Color: Newly unrolled leaf, adaxial: 144A. Newly unrolled leaf, abaxial: 144B. Mature leaf, adaxial: Geniculum varies between 144A, 146A and intermediate colors. 144A below geniculum. Mature leaf, abaxial: Geniculum 144A or between 144A and 144B. Below geniculum 144B, proximally slightly darker, 144A at the base.

*Leaf blade.*—Shape: Ovate; apex long, acuminate; base cordate; margin entire. Size: About 16.6 cm long, about 10.6 cm wide; length : width ratio about 1.6:1. Aspect: Most leaves approximately horizontal; some slightly oblique with apices pointing slightly down; almost flat with lobes slightly curving upwards. Texture/surface: Thick, leathery, glabrous, glossy; young leaves very glossy. Venation: Pinnipalmate; midrib protrudes from adaxial and abaxial surfaces; primary veins are sunken in adaxial surface and protrude from abaxial surface. Color: Newly unrolled leaf, adaxial: Much darker than 144A, more green and slightly lighter than 146A. Slight brownish anthocyanin coloration sometimes present on midrib. Newly unrolled leaf, abaxial: Varies between 146B and 146C. Brownish anthocyanin coloration often present on veins. Mature leaf, adaxial: Varies between 147A and a color slightly lighter and more yellow than 147A. Proximal portions of primary veins and more than half of midrib between 144A, 146A and 146B. Some brownish anthocyanin coloration often present near petiole juncture and extends onto proximal portion of midrib. Mature leaf, abaxial: Greener than 146B. Proximal portions of primary viens and more than half of midrib slightly more yellow than 146D.

Inflorescence description:

*Inflorescence arrangement*.—Spathes with spadices held high above foliage, usually in the center of the plant. Peduncles almost vertical, usually straight. Most mature spathes approximately horizontal, convex, with an apex pointing downwards; some oblique, at approximately 45° from vertical, cupped with an apex pointing to the side or slightly up. Most spadices approximately vertical, in straight line with peduncle; some slightly leaning towards spathe.

*Flowering*.—Abundant and year-round. Flowers naturally in 15-cm containers about 13 months after planting tissue culture-produced microcuttings. At 14.5 months about 5.3 inflorescences per plant.

*Spathe longevity*.—Spathe remains red and glossy for at least 9 weeks following bud appearance among foliage.

*Peduncle*.—Size: About 27.4 cm long, about 3.1 mm in diameter immediately below spathe. About 3.1 mm of peduncle between spathe and spadix base in front. Stipe about 1–2 mm. Color: Just before spathe unrolling: Varies between 146A, 146B, 144A and intermediate colors. Proximal portion slightly lighter than distal. Usually some red coloration immediately below spathe, especially in the back. Mature inflorescence: Most of peduncle is green, similar to 144A. Various portions, usually in distal half, have variable degrees of brownish anthocyanin coloration mixed with green. Sometimes the front area immediately below spathe becomes relatively dark and may be similar to one of the different combinations of the following colors: 178A, 178B, 174A, 176A and/or 176B. The back area immediately below spathe is often more reddish and less brownish. The front section between spathe and spadix base, orange red. The amount of brownish anthocyanin coloration on peduncles tends to increase with subsequent inflorescence development.

*Spathe*.—Shape: Ovate; apex between acuminate and aristate; base cordate; margin entire. Size: About 6.1 cm long, about 4.9 cm wide; ratio length: width about 1.2:1. Texture/Surface: Glabrous; exceptionally glossy; non-puckered. Color: Closed bud (before unrolling): Approximately 146A with a darker margin (approximately 185A) and yellow-green apex (between 150A and 154A). Newly unrolled spathe, front surface: More red than 185A, much darker than 46A. Newly unrolled spathe, back surface: Approximately 46A with a darker margin (approximately 185A) and yellow-green apex (between 150A and 154A). Mature spathe, front surface: Most similar to, but more red than 185A; much darker than 53A. With subsequent development spathe becomes progressively darker. Mature spathe, back surface: Approximately 46A with a darker margin (approximately 185A) and yellow-green apex (between 150A and 154A).

*Spadix*.—Shape: Cylindrical, straight, very slightly tapering at apex; cross section rounded. Size: About 3.4 cm long, about 6.3 mm in diameter. Flower density: About 8 to 10 flowers per linear centimeter of spadix (mid-section). Color: Young, immediately after spathe unrolling: Between 11A, 8A and 7B, except for the most proximal portion, which is slightly lighter and starts turning whitish shortly after spathe unrolling. Mature inflorescence: Proximal zone, with pistils, varies between 158C and 159D. Distal zone, without pistils, between 11A, 7A and 7B. After all pistils protrude entire spadix becomes white (between 158C and 158D). With subsequent development, starting from spadix base, perianth becomes purple (185C), but pistils remain whitish. Eventually, perianth is darker than 185C on the entire spadix length, except for apex.

*Botanical flower*.—Perianth: Perianth of an individual flower appears on the spadix surface as almost a diamond shape, about 2.5 to 3 mm long and 2 mm wide. Pistil: About 2 mm long; cross-section rectangular, about 0.8 mm by 0.6 mm; protrudes fraction of a mm beyond perianth; cream, translucent. Stigma minute. Stamens: About 1.2 mm long and 0.7 mm wide; cream, translucent; flat; firmly pressed against pistil. Do not protrude beyond perianth until pollen dehiscence. Pollen: Scarce amount of whitish pollen rarely produced. Frangrance: not detected.

*Seed*.—Spontaneous seed development rarely observed.

Roots description: Main roots relatively thick, fleshy, cream to light brown with yellow root caps. Abundant lateral roots.

Disease and insect resistance: Plants of 'Lola', which are grown in commercial greenhouses, have not shown any unusual susceptibility to pathogens or insects common to Anthurium.

I claim:

1. A new and distinct cultivar of Anthurium plant named 'Lola' as dsecribed and illustrated herein.

* * * * *